United States Patent
Jo et al.

(10) Patent No.: US 9,869,631 B2
(45) Date of Patent: Jan. 16, 2018

(54) ANALYSIS DEVICE AND METHOD OF DETERMINING MOUNTED STATE OF CARTRIDGE OF THE ANALYSIS DEVICE

(71) Applicant: SAMSUNG ELECTRONICS CO., LTD., Suwon-si (KR)

(72) Inventors: Jeong-min Jo, Suwon-si (KR); Tae-soo Kim, Yongin-si (KR); Sung-hwa Lee, Anyang-si (KR); Hyun-soo Jang, Uiwang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 456 days.

(21) Appl. No.: 14/563,318

(22) Filed: Dec. 8, 2014

(65) Prior Publication Data

US 2015/0211994 A1    Jul. 30, 2015

Related U.S. Application Data

(60) Provisional application No. 61/977,987, filed on Apr. 10, 2014.

(30) Foreign Application Priority Data

Jan. 29, 2014    (KR) .......................... 10-2014-0011732

(51) Int. Cl.
*G01N 21/59*    (2006.01)
*G01N 21/13*    (2006.01)

(52) U.S. Cl.
CPC ..... *G01N 21/13* (2013.01); *G01N 2201/0256* (2013.01)

(58) Field of Classification Search
CPC ............... G01N 21/59; G01N 2201/12; G01N 2201/061
USPC ............................................... 250/206, 559.3
See application file for complete search history.

(56) References Cited

U.S. PATENT DOCUMENTS

| 5,225,691 | A | * | 7/1993 | Powers | ............. | H01L 21/67265 |
| | | | | | | 250/223 R |
| 5,949,611 | A | * | 9/1999 | Stephens | ............ | G11B 15/6751 |
| | | | | | | 360/96.51 |
| 2006/0256336 | A1 | * | 11/2006 | Fritz | .................... | G01B 11/272 |
| | | | | | | 356/399 |
| 2008/0195020 | A1 | | 8/2008 | Cabuz et al. | | |
| 2013/0210126 | A1 | * | 8/2013 | Williams | ................. | C12O 1/68 |
| | | | | | | 435/287.2 |
| 2015/0132860 | A1 | * | 5/2015 | Cook | ................ | G01N 35/1079 |
| | | | | | | 436/501 |

\* cited by examiner

*Primary Examiner* — Seung C Sohn
(74) *Attorney, Agent, or Firm* — Sughrue Mion, PLLC

(57) ABSTRACT

Disclosed are an analysis device and a method of determining a mounted state of a cartridge mounted in the analysis device. The analysis device includes: a mounting unit configured to mount a cartridge on which at least one well for containing a specimen is formed; a measuring unit configured to measure at least one signal corresponding to the at least one well formed on the cartridge; and an operation processor configured to process the at least one measured signal with respect to the at least one well measured by the measuring unit, wherein the operation processor determines a mounted state of the cartridge based on the at least one measured signal with respect to the at least one well formed on the cartridge.

21 Claims, 5 Drawing Sheets

ANALYSIS DEVICE AND METHOD OF DETERMINING MOUNTED STATE OF CARTRIDGE OF THE ANALYSIS DEVICE

RELATED APPLICATIONS

This application claims priority from Korean Patent Application No. 10-2014-0011732, filed on Jan. 29, 2014, in the Korean Intellectual Property Office, and the benefit of U.S. Provisional Patent Application No. 61/977,987, filed on Apr. 10, 2014, in the U.S. Patent and Trademark Office, the disclosures of which are incorporated herein in their entireties by reference.

BACKGROUND

1. Field

Apparatuses and methods consistent with exemplary embodiments relate to an analysis device and a method of determining a mounted state of a cartridge of the analysis device; and more particularly, to an analysis device for analyzing a specimen contained in a cartridge that is mounted in the analysis device and to a method of determining a state that the cartridge is mounted in the analysis device.

2. Description of the Related Art

An analysis device for inspecting and analyzing a specimen generally includes a cartridge for containing the specimen. For example, an analysis device, such as an in vitro diagnosis inspecting device, uses a cartridge into which a specimen having biological information such as a gene is injected. The cartridge may include a specimen injecting portion, i.e., a portion into which a specimen is injected, and a chamber for containing a reagent. During inspection, the cartridge is mounted in the in vitro diagnosis inspecting device, and the specimen is moved to the chamber containing the reagent to be reacted with the reagent. A reactant resulting from a reaction between the specimen and the reagent is measured using an optical signal, and a measured result is thus obtained.

The cartridge may be designed to accurately move the specimen and to be accurately positioned in the analysis device for accurately measuring the reactant in the chamber. To accurately move the specimen and to be accurately positioned in the analysis device, an analysis device of the related art includes a sensor for determining whether a cartridge is mounted, but the sensor does not often accurately detect a mounted state of the cartridge, and thus inaccurate inspection results may be obtained. Even if the analysis device of the related art is provided with an additional sensor to improve accuracy of detecting the mounted state of the cartridge, an increased product cost results.

SUMMARY

One or more exemplary embodiments may provide an analysis device that inspects and analyzes a specimen contained in a cartridge that is mounted in the analysis device.

One or more exemplary embodiments may provide a method of accurately determining a state for the cartridge to be mounted in the analysis device.

Additional exemplary aspects will be set forth in part in the description which follows and, in part, will be apparent from the description, or may be learned by practice of the presented embodiments.

According to an aspect of an exemplary embodiment, an analysis device includes: a mounting unit configured to receive a cartridge on which at least one well for containing a specimen is formed; a measuring unit configured to measure a signal corresponding to the at least one well formed on the cartridge; and an operation processor configured to process the measured signal with respect to the at least one well measured by the measuring unit, wherein the operation processor determines a mounted state of the cartridge based on the measured signal with respect to the at least one well formed on the cartridge. The at least one well may be a plurality of wells, the at least one signal may be a plurality of signals corresponding to the plurality of wells, and the operation processor may determine the mounted state based on a deviation among the plurality of signals.

The at least one signal may be an optical signal with respect to the at least one well formed on the cartridge. For example, the measuring unit may include a light source unit configured to sequentially scan and irradiate light to the at least one well formed on the cartridge, and a photodetector configured to detect an optical signal from the light irradiated to the at least one well formed on the cartridge.

The light source unit may include a sub-wavelength light source that irradiates light having a wavelength band that is unaffected by a reagent and a specimen contained in the at least one well; the measured signal is used in the determining of the mounted state of the cartridge and is optical signal obtained from the light irradiated by the sub-wavelength light source.

The plurality of wells may include a specimen well and a reference measurement well; the measuring unit may measure a signal with respect to the specimen well and signal with respect to the reference measurement well; the operation processor may determine the mounted state of the cartridge based on a deviation of the measured signal with respect to the specimen well and the measured signal with respect to the reference measurement well.

The operation processor may determine the mounted state of the cartridge based on at least one of: a difference between absolute values of the plurality of measured signals, a ratio of a maximum value of the plurality of measured signals to a minimum value of the plurality of measured signals, a difference between the maximum value and the minimum value, an average deviation of the plurality of measured signals, and a standard deviation of the plurality of measured signals.

The operation processor may determine the mounting state based on all or some of the plurality of signals.

When the deviation of the plurality of signals is in a reference range, the operation processor may determine that the cartridge is properly mounted, and when the deviation of the plurality of measured signals is outside the reference range, the operation processor may determine that the cartridge is improperly mounted.

The analysis device may further include a memory configured to store information with respect to a kind of the cartridge; the operation processor may set a reference, which is used in the determining of the mounted state of the cartridge, according to the information stored in the memory with respect to the kind of the cartridge.

The analysis device may further include a display unit configured to display the mounted state of the cartridge.

According to an aspect of another exemplary embodiment, a method of determining a mounted state of a cartridge of an analysis device includes: mounting a cartridge on which at least one well for containing a specimen is formed in the analysis device; measuring a signal corresponding to the at least one well formed on the cartridge; and determining a mounted state of the cartridge based on the measured signal with respect to the at least one well. The measured signal may be a plurality of measured signals and the method may further include calculating a deviation among the plurality of measured signals and determining the mounted state based on the deviation.

The measured signal with respect to the at least one well formed on the cartridge may include an optical signal.

The measuring of the signal corresponding to the at least one well formed on the cartridge may include: sequentially scanning and irradiating light to the at least one well formed on the cartridge; detecting an optical signal from the light irradiated to the at least one well formed on the cartridge.

The measured signal may be used in the determining of the mounted state of the cartridge and may be optical signal obtained from a light with a wavelength that is unaffected by a reagent and a specimen contained in the at least one well.

The analysis device may include a reference measurement well; the plurality of measured signals may include a measured signal with respect to the reference measurement well of the analysis device; the calculating of the deviation among the plurality of measured signals may comprise calculating a deviation of a signal including a measured signal with respect to the at least one well and a measured signal with respect to the reference measurement well.

The determining the mounted state may include determining the mounted state based on at least one of: a difference among absolute values of the plurality of measured signals, a ratio of a maximum value of the plurality of measured signals to a minimum value of the plurality of measured signals, a difference between the maximum value and the minimum value, an average deviation of the plurality of measured signals, and a standard deviation of the plurality of measured signals.

The deviation among the plurality of measured signals may include a deviation between at least two of the plurality of measured signals.

The determining of the mounted state of the cartridge may include determining that the cartridge is properly mounted when the deviation of the measured signal is in a reference range, and determining that the cartridge is improperly mounted when the deviation of the measured signal is outside the reference range.

The method may further include storing, in a memory, information with respect to a kind of the cartridge; the determining of the mounted state of the cartridge may include setting a reference, which is used in the determining of the mounted state of the cartridge, according to the information stored in the memory with respect to the kind of the cartridge.

The method may further include displaying the mounted state of the cartridge.

According to the above described method of an exemplary embodiment of the present disclosure, it may be possible to detect an accurate mounted state of the cartridge by using the existing measuring unit of the analysis device without additional cost.

BRIEF DESCRIPTION OF THE DRAWINGS

These and/or other exemplary aspects and advantages will become apparent and more readily appreciated from the following description of exemplary embodiments, taken in conjunction with the accompanying drawings in which.

DETAILED DESCRIPTION

Figure 1:
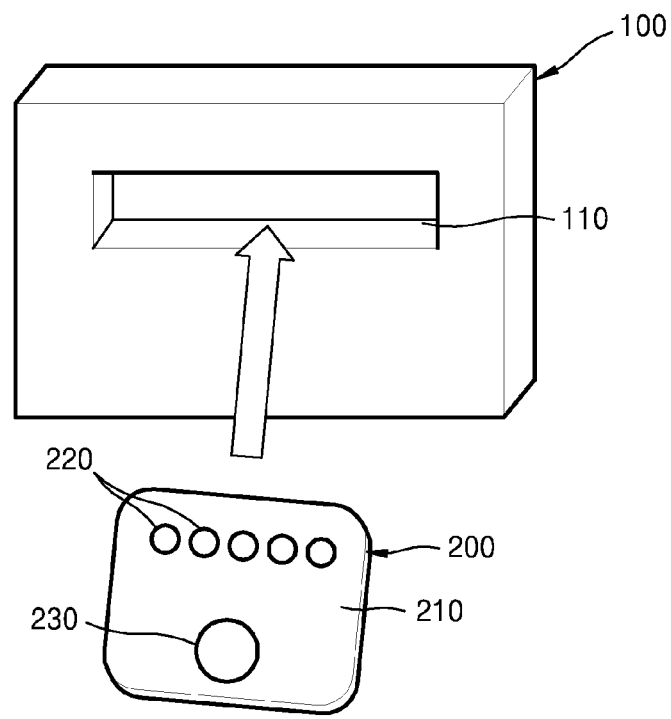
FIG. 1 is a schematic diagram of an analysis device according to an exemplary embodiment.

The present disclosure and methods of accomplishing the same may be understood more readily by reference to the following detailed description of exemplary embodiments and the accompanying drawings. However, the present disclosure may be embodied in many different forms, and should not be construed as being limited to the embodiments set forth herein. Rather, these embodiments are provided so that this disclosure will be thorough and complete and will fully convey the concept of the invention to those skilled in the art, and the present disclosure will only be defined by the appended claims. Like reference numerals refer to like elements throughout the specification.

The terminology used herein will be described briefly, and the present disclosure will be described in detail.

The terminology used herein is defined in consideration of the function of corresponding components used in the present disclosure and may be varied according to users, operator's intention, or practices. In addition, an arbitrary defined terminology may be used in a specific case and will be described in detail in a corresponding description paragraph. Therefore, the terminology used herein is for the purpose of describing particular embodiments only and is not intended to be limiting of the invention.

In addition, unless explicitly described to the contrary, the word "comprise" and variations such as "comprises" or "comprising" will be understood to imply the inclusion of stated elements but not the exclusion of any other elements. Expressions such as "at least one of," when preceding a list of elements, modify the entire list of elements and do not modify the individual elements of the list.

The present disclosure will be described more fully hereinafter with reference to the accompanying drawings, in which exemplary embodiments of the invention are shown. As those skilled in the art would realize, the described embodiments may be modified in various different ways, all without departing from the spirit or scope. The drawings and description are to be regarded as illustrative in nature and not restrictive.

Figure 2:
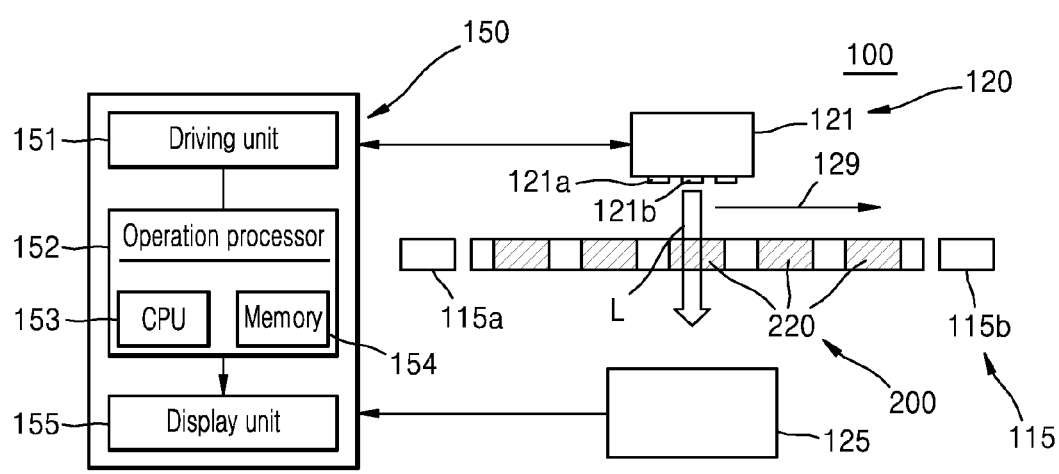
FIG. 2 is a block diagram of a measuring unit and a circuit unit included in the analysis device shown in FIG. 1.

FIG. 1 schematically shows an outer appearance of an analysis device according to an exemplary embodiment; FIG. 2 is a block diagram of a measuring unit and a circuit unit included in the analysis device shown in FIG. 1.

Referring to FIG. 1 and FIG. 2, an analysis device 100 includes a mounting unit 110 into which a cartridge 200 is insertable. The analysis device 100 includes a measuring unit 120 for measuring the inserted cartridge 200 and a circuit unit 150 for processing signals measured by the measuring unit 120.

Since the mounting unit 110 may be configured such that the cartridge 200 may be inserted therein and mounted thereto, various structures of the mounting unit may be changed depending on various structures of the cartridge 200. For example, the mounting unit 110, as shown in FIG.

1, may be slot shaped or may be configured to enable docking with the cartridge in another manner. The mounting unit 110 is provided with reference measurement wells 115 formed thereon. For example, a first reference measurement well 115a and a second reference measurement well 115b are disposed on opposite sides of the cartridge 200.

The cartridge 200 may be a lab-on-a chip which includes a flat plate case 210 and one or more wells 220 formed on one side of the flat plate case 210. The wells 220 may be arranged in a straight line. Though the wells 220 are arranged in a straight line in FIG. 1, the wells 220 may be arranged in multiple rows. Each of the wells contains a specimen. The wells 220 may be previously filled with reagent used for reacting with a specimen to be inspected. In addition, the cartridge 200 may include a specimen injecting portion 230 into which the specimen is injected. The cartridge 200 may include micro-paths (not shown) to move a fluid-type specimen injected into the specimen injecting portion 230 to the wells 220. The analysis device 100 according to an exemplary embodiment may be used in various fields such as environmental monitoring, food inspection, and medical diagnostics. The specimen may be varied according to a desired use. For example, the specimen may be fluid such as blood, and in this case the analysis device 100 may be an in vitro diagnostic apparatus for analyzing blood.

The measuring unit 120 may include a light source unit 121 that sequentially irradiates light to the cartridge 200, and a photodetector 125 that detects light transmitted through the cartridge 200. The light source unit 121 and the photodetector 125 are provided at opposite sides, such that an inserted cartridge 200 will be disposed therebetween. Light irradiated by the light source unit 121 is transmitted to wells 220 of the cartridge 200. The light source unit 121 and the photodetector 125 sequentially scan the wells 220 of the cartridge 200 while being moved together in one direction 129 (hereinafter, referred to as a scan direction) by a driving device (not shown). In addition, the light source unit 121 and the photodetector 125 may scan the reference measurement wells 115 formed on the mounting unit 110. According to another exemplary aspect, while the light source unit 121 and the light detector 125 are fixed, the cartridge 200 may be moved and scanned.

The light source unit 121 includes a main wavelength light source 121a and irradiates a light L into the wells 220 of the cartridge 200. The main wavelength light source 121a is used to inspect the specimen contained in the cartridge 200. The main wavelength light source 121a may be a light source that emits light having a wavelength band selected from electromagnetic waves having various wavelengths, such as microwaves, infrared rays, a visible ray, ultraviolet rays, and X-rays. For example, the main wavelength light source 121a indicates optical feature according to the density of the specimen in the cartridge 200, or irradiates light having a wavelength causing a change of absorbance according to a reaction with a reagent. One or more main wavelength light sources 121a may be used. The main wavelength light source 121a may be formed of one or more light sources having different respective wavelength bands in order to simultaneously detect optical characteristics of the specimen contained in the cartridge 200 by using the light sources, thereby being able to simultaneously detect various detecting items. The light source unit 121 may further include a sub-wavelength light source 121b. The sub-wavelength light source 121b may irradiate light having a wavelength band with an optical characteristic that is constant regardless of the density of the specimen in the cartridge 200 or light having a wavelength band that does not cause a change of absorbance according to reaction with a reagent. The sub-wavelength light source 121b may be used to determine whether the cartridge 200 is mounted or not and whether the cartridge 200 is properly mounted or not, which will be described below. In addition, the sub-wavelength light source 121b may be used to correct an error associated with a result measured by the main wavelength light source 121a.

The light source unit 121 may further include a lens for focusing light irradiated from the main wavelength and sub-wavelength light sources 121a and 121b and an aperture limiting the amount of light that passes therethrough, so that spots of light formed on the wells 220 of the cartridge 200 by the light irradiated by the light source unit 121 may be made to be smaller than diameters of the wells 220 of the cartridge 200.

The light detector 125 detects the light L that is irradiated into the wells 220 of the cartridge 200 and is transmitted therethrough. The light detector 125 may be a light-receiving device such as a photodiode or an image sensor.

The circuit unit 150 may include a driving unit 151 configured to drive and control the measuring unit 120, an operation processor 152 configured to process optical signals measured by the measuring unit 120, and a display unit 155 configured to display information processed in the operation processor 152.

The operation processor 152 may include a central processing unit (CPU) 153 and a memory 154. The signals measured by the measuring unit 120 are stored in the memory 154. The CPU 153 calculates a deviation between the signals measured by measuring unit 120, and determines a mounted state of the cartridge 200 by using the calculated deviation. Since optical characteristics of light passing through the wells 220 may vary according to the kind of the cartridge 200, the mounted state of the cartridge 200 may be determined based on the kind of the cartridge 200. Therefore, information indicating the kind of cartridge 200 may be stored in the memory 154. The information indicating the kind of cartridge 200 may manually be input when the cartridge 200 is inserted and mounted in the mounting unit 110, or automatically input using an identification mark that is attached on the cartridge 200 and recognizable by the measuring unit 120 or a sensor.

A method in which the operation processor 152 determines the mounted state of the cartridge 200 will be described in detail.

Hereinafter, referring to FIGS. 3A, 3B, 4A and 4B, a method of determining a mounted state of a cartridge of an analysis device according to an exemplary embodiment will be described.

Figure 3A:
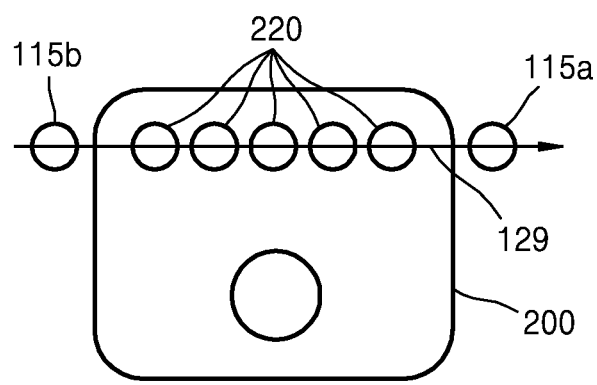
FIG. 3A is a schematic diagram showing a cartridge that is properly mounted.
Figure 3B:
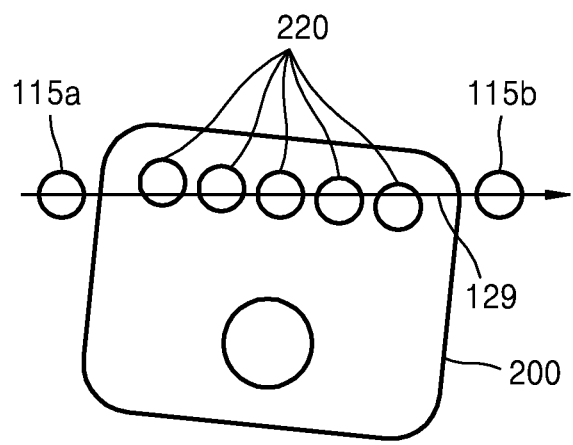
FIG. 3B is a schematic diagram showing a cartridge that is improperly mounted.

FIG. 3A is a schematic diagram showing that the cartridge 200 is properly mounted, and FIG. 3B is a schematic diagram showing that the cartridge 200 is improperly mounted.

As shown in FIG. 3A, when the cartridge 200 is properly mounted, a scanning direction 129 of the measuring unit 200 is positioned at the respective centers of the first and second reference wells 115a and 115b and the wells 220 of the cartridge 200. In contrast, as shown in FIG. 3B, when the cartridge 200 is improperly mounted, the scanning direction 129 of the measuring unit 200 is positioned at the respective centers of the first and second reference wells 115a and 115b but does not pass through the respective centers of the wells 220 of the cartridge 200.

Figure 4A:
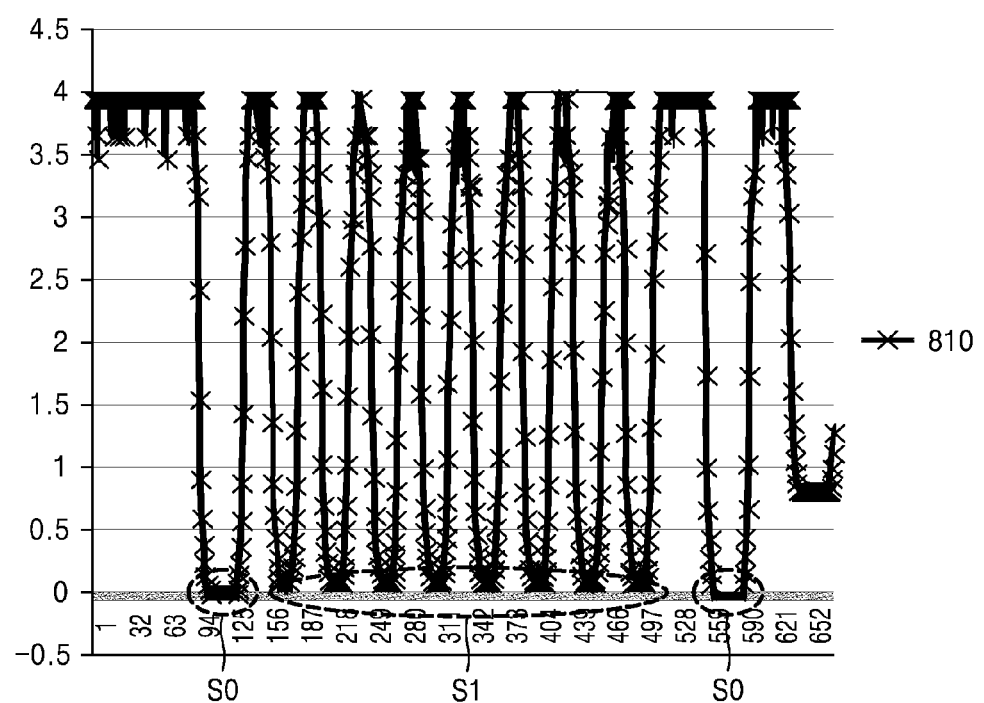
FIG. 4A is a graph showing optical data when a cartridge is properly mounted.
Figure 4B:
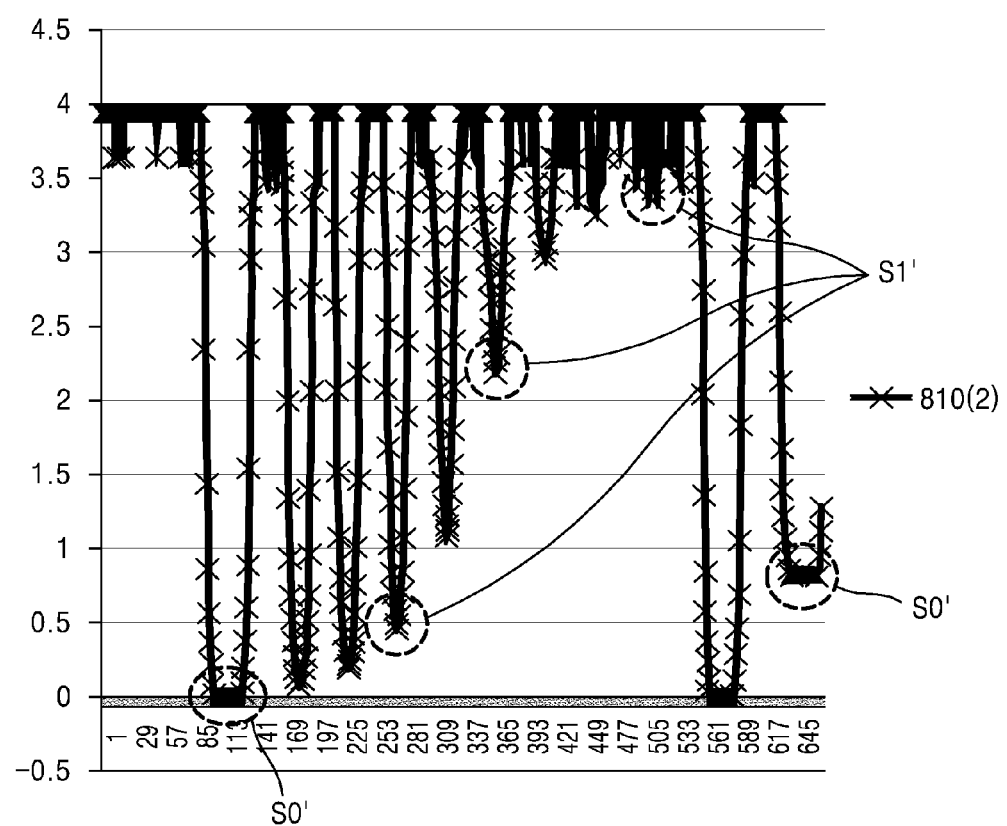
FIG. 4B is a graph showing optical data when a cartridge is improperly mounted.

FIG. 4A is a graph showing optical data when the cartridge 200 is properly mounted, and FIG. 4B is a graph showing optical data when the cartridge 200 is improperly mounted. The optical data shown in FIGS. 4A and 4B is obtained by using the sub-wavelength light source 121b that irradiates light having a wavelength band with an optical characteristic that is constant regardless of the density of the specimen of the cartridge 200 or light having a wavelength band that does not cause a change of absorbance according to reaction with a reagent.

As shown in FIG. 4A, when the cartridge 200 is properly mounted, all of measured signals S1 with respect to the wells 220 of the cartridge 200 may be identical to one another. In addition, by using the sub-wavelength light source 121b, even if the wells 220 of the cartridge 200 contain specimens, measured signals S0 of light directed to the first and second reference wells 115a and 115b may be identical to the measured signals S1 of light directed to the wells 220.

When the cartridge 200 is improperly mounted, since the scanning direction 129 does not pass through the centers of the wells 220 as shown in FIG. 3B, measured signals S1' of light directed to the wells 220 of the cartridge 200 may be different from one another as shown in FIG. 4B. In addition, measured signals S0' of light directed to the first and second reference wells 115a and 115b may be different from the measured signals S1'.

Since the first and second reference wells 115a and 115b are constantly measured by the measuring unit 120 regardless of the mounted state of the cartridge 200, measured signals S0' with respect to the first and second reference wells 115a and 115b of a case in which the cartridge 200 is improperly mounted may be equal to measured signals S0 with respect to the first and second reference wells 115a and 115b of a case in which the cartridge 200 is properly mounted.

Accordingly, based on the deviation of the measured signals S0 and S0' with respect to the first and second reference wells 115a and 115b and the measured signals S1 and S1' with respect to the wells 220 of the cartridge 200, the mounted state of the cartridge 200 may be determined.

For example, if an allowed signal range is set for determining a properly mounted state of the cartridge 200 based on the measured signals S0 and S0' with respect to the first and second reference wells 115a and 115b, then by determining whether the measured signals S1 and S1' with respect to the wells 220 of the cartridge 200 are within the allowed signal range, it is possible to thereby determine whether the mounted state of the cartridge 200 is proper.

In another example, whether the mounted state of the cartridge 200 is proper may be determined based on a difference between absolute values, a ratio of a maximum value to a minimum value, a difference between the maximum value and the minimum value, an average deviation, and a standard deviation, of signals measured when the cartridge 200 is properly mounted. In other words, as shown in FIG. 4B, when the cartridge 200 is improperly mounted, since the measured signals S0' with respect to the first and second reference wells 115a and 115b are different from the measured signals S1' with respect to the wells 220 of the cartridge 200, a difference of absolute values, a ratio of the maximum and minimum value, a difference between absolute values, a ratio of a maximum value to a minimum value, a difference between the maximum value and the minimum value, an average deviation, and a standard deviation, of signals measured when the cartridge 200 is improperly mounted (i.e., in the improperly mounted state) are different from those of when the cartridge 200 is properly mounted. Accordingly, if allowed ranges with respect to a difference between absolute values, a ratio of a maximum value to a minimum value, a difference between the maximum value and the minimum value, an average deviation, and a standard deviation, of measured signals are set, it is possible to determine whether the difference between absolute values, the ratio of the maximum value to the minimum value, the difference between the maximum value and the minimum value, the average deviation, and the standard deviation, of measured signals are within the allowed ranges, thereby determining whether the mounted state of the cartridge 200 is proper or improper. Since the measured signals S1' with respect to the wells 220 of the cartridge 200 are different from one another when the cartridge 200 is improperly mounted, whether the cartridge 200 is properly mounted may be determined by using a deviation of the measured signals S1'.

In another example, when the measured signals S1 and S1' with respect to the wells 220 of the cartridge 200 are not detected, it may be determined that the cartridge 200 is not mounted. A separate sensor, configured to determine whether the cartridge 200 is mounted in the analysis device 100, may be further provided therewith.

Figure 5:
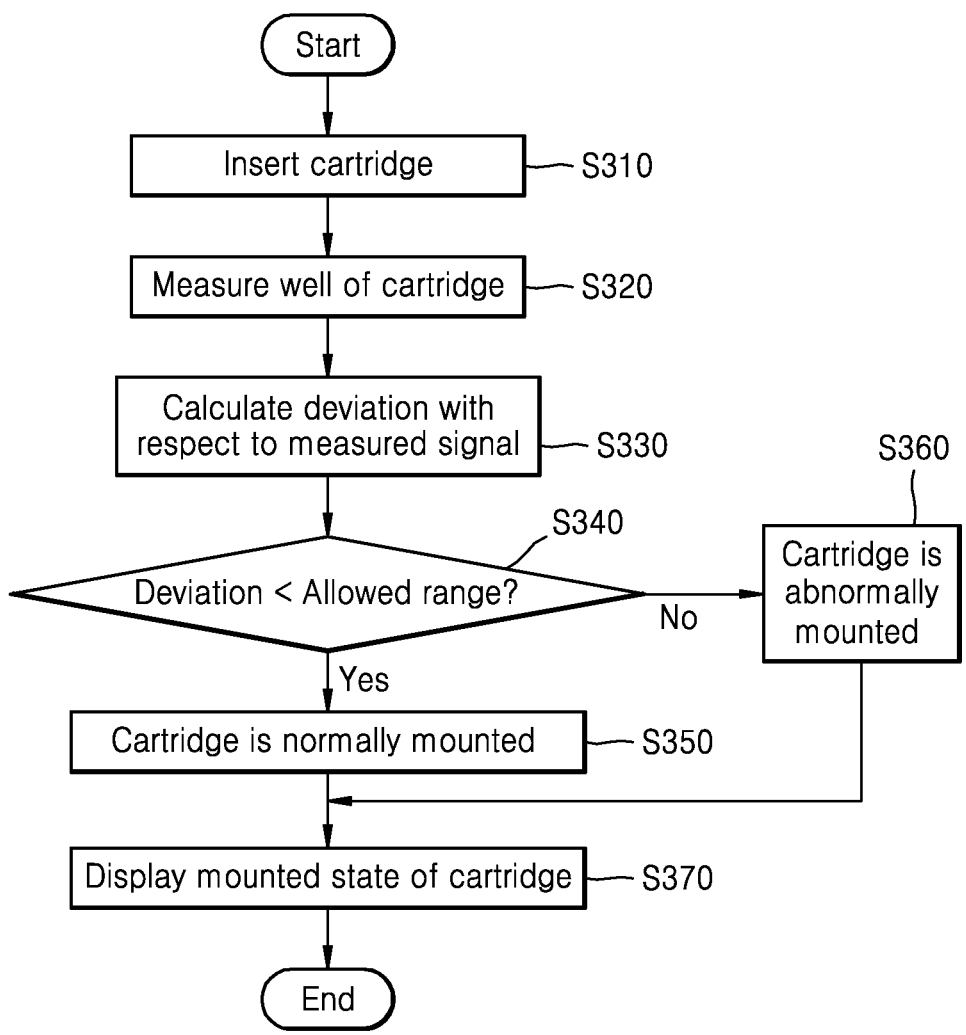
FIG. 5 shows a flowchart of a method of determining a mounted state of a cartridge of an analysis device according an exemplary embodiment.

FIG. 5 shows a flowchart of a method of determining a mounted state of the cartridge 200 of the analysis device 100 according to an exemplary embodiment.

Referring to FIG. 5, the cartridge 200 is first inserted into the mounting unit 110 of the analysis device 100 at S310.

When the cartridge 200 is inserted and mounted in the mounting unit 110, the measuring unit 120 of the analysis device 100 is driven and measures signals with respect to the wells 220 of the cartridge 200 at S320. As described above, if the light source unit 121 of measuring unit 120 includes the sub-wavelength light source 121b, light may be irradiated by the sub-wavelength light source 121b into the wells 220 of the cartridge 200, and the light irradiated by the sub-wavelength light source 121b may be detected. As described above, if the mounting unit 110 is provided with reference measurement wells 115, that is, the first and second reference wells 115a and 115b, the measuring unit 120 of the analysis device 100 may measure signals with respect to the reference measurement wells 115.

The measured signals may be stored in the memory 151.

The operation processor 150 of the analysis device 100 calculates various deviations of the measured signals with respect to the wells 220 of the cartridge 200 at S330. The light source unit 121 of the analysis device 100 may be driven to acquire one or more measured signals with respect to the wells 220 of the cartridge 200, and thus a representative measured signal value with respect to each of the wells 220 may be obtained. The representative measured signal value may be, for example, a peak value or an average value of the respective values of the signals with respect to each of the wells 220. The deviations may be calculated including the measured signals with respect to the wells 220 of the cartridge 200 as well as the measured signals with respect to the reference measurement wells 115.

The operation processor 152 of the analysis device 100 determines a mounted state of the cartridge 200 by determining whether the deviations of the measured signals are within the allowed range at S340. The allowed range of a reference for determining the mounted state of the cartridge 200 may be adjusted by a user. As described above, when the cartridge 200 is properly mounted, since the measured signals with respect to the reference measurement wells 115 are constant, even if a deviation of the measured signals with respect to the reference measurement wells 115 occurs (i.e., the measured signals with respect to the reference measurement wells 115 deviate from), since the deviation is within the corresponding allowed range, it may be determined that the cartridge 200 is properly mounted when the measured signals with respect to the wells 220 of the cartridge 200 are within the corresponding allowed ranged at S350. In contrast, when the cartridge 200 is improperly mounted, since a deviation of the measured signals with respect to the reference measurement wells 115 occurs, it may be determined that the cartridge 200 is improperly mounted when the measured signals with respect to the wells 220 of the cartridge 200 are outside the corresponding allowed ranged at S350.

The mounted state of the cartridge 200 is displayed based on the determination of the mounted state of the cartridge 200 at S370. For example, when the cartridge 200 is improperly mounted, the improperly mounted state of the cartridge 200 may be indicated by flickering a lamp (not shown).

When the cartridge 200 is inserted, information with respect to a kind of the cartridge 200 may manually be input. In this case, when the mounted state of the cartridge 200 is determined, the allowed range used as reference for determining the mounted state of the cartridge 200 may be adjusted according to the kind of the cartridge 200.

A case in which the sub-wavelength light source 121*b* of the light source unit 121 is used to determine the mounted state of the cartridge 200 has been exemplified in the above described exemplary embodiment, but the determining of the mounted state of the cartridge 200 is not limited thereto. Even if the main wavelength light source 121*a* is used, since optical signals with respect to the wells 220 of the cartridge 200 may vary according to the mounted state of the cartridge 200, the mounted state of the cartridge 200 may be determined based on optical signals associated with the main wavelength light source 121*a*.

A case in which the cartridge 200 is a card type of cartridge, i.e., a lab-on-a chip, has been exemplified in the described exemplary embodiment, but the type of cartridge is not limited thereto. For example, the cartridge 200 may be a disk type of cartridge, i.e., a lab-on-a-CD, in which one or more wells are circumferentially formed on an edge of a disk type of substrate. When the cartridge 200 is a disk type of cartridge, i.e., the lab-on-a-CD, while the measuring unit 120 of the analysis device 100 remains fixed, the cartridge 200 may be rotated so that the wells of the cartridge 200 may be scanned. Even in this case, it would be easily understood to those skilled in the art that the mounted state of the cartridge 200 may be determined based on the measured signals with respect to the wells 220 of the cartridge 200.

In addition, a case in which the photodetector 125 of the analysis device 100 detects the light passing through the wells 220 of the cartridge 200 has been exemplified in this exemplary embodiment, but the photodetector 125 is not limited thereto. For example, the photodetector 125 may also be used to determine the mounted state of the cartridge 200 in a case in which the analysis device analyzes a light reflected by the wells 220 of the cartridge 200.

A case in which the analysis device 100 detects the optical signal through the measuring unit 120 has been exemplified in this exemplary embodiment, but the analysis device 100 is not limited thereto. For example, the analysis device 100 may be one that detects an electrical signal or a thermal signal with respect to the wells 220 of the cartridge 200 and determines the mounted state of the cartridge 200 based on the electrical signal or the thermal signal.

While exemplary embodiments have been described in connection with the figures, it is to be understood that these embodiments and figures are not to be considered to be limiting, and, on the contrary, are intended to cover various modifications and equivalent arrangements included within the spirit and scope of the appended claims.

What is claimed is:

1. An analysis device, comprising:
   a mounting unit configured to receive a cartridge on which at least one well for containing a specimen is formed;
   a measuring unit configured to measure at least one signal corresponding to the at least one well formed on the cartridge; and
   an operation processor configured to process the at least one measured signal with respect to the at least one well measured by the measuring unit,
   wherein the operation processor configured to determine a mounted state of the cartridge based on the at least one measured signal, and
   wherein the at least one well comprises a plurality of wells, the at least one signal comprises a plurality of signals, and the operation processor is configured to determine the mounted state of the cartridge based on a deviation among the plurality of signals.

2. The analysis device of claim 1, wherein the at least one signal is at least one optical signal.

3. The analysis device of claim 2, wherein the measuring unit comprises a light source unit configured to irradiate light to the at least one well formed on the cartridge, and a photodetector configured to detect the at least one optical signal from the light irradiated to the at least one well formed on the cartridge.

4. The analysis device of claim 3, wherein the light source unit comprises a first light source configured to emit a first wavelength band of light and a second light source configured to emit a second wavelength band of light, different from the first wavelength band, wherein the second wavelength band is unaffected by a reagent and a specimen contained in the at least one well;
   wherein the operation processor is configured to determine the mounted state of the cartridge based on the at least one measured signal obtained from the light irradiated by the second light source.

5. The analysis device of claim 1, wherein:
   the plurality of wells comprises a specimen well and a reference measurement well; and
   the operation processor is configured to determine the mounted state of the cartridge based on a deviation between a measured signal with respect to the specimen well and a measured signal with respect to the reference measurement well.

6. The analysis device of claim 1, wherein the at least one measured signal comprises a plurality of measured signals, and the operation processor is configured to determine the mounted state of the cartridge based on at least one of: a difference in absolute values among the plurality of measured signals; a ratio of a maximum value among the plurality of measured signals to a minimum value among the plurality of measured signals; a difference between the maximum value among the plurality of measured signals and the minimum value among the plurality of measured signals; an average deviation of the plurality of measured signals; and a standard deviation of the plurality of measured signals.

7. The analysis device of claim 1, wherein the at least one signal comprises the plurality of signals, respectively corresponding to the plurality of wells, and the operation processor is configured to determine the mounted state of the cartridge based on at least one of a plurality of measured signals.

8. The analysis device of claim 1, wherein when the deviation among the plurality of signals is within a reference range, the operation processor determines that the cartridge is properly mounted, and when the deviation among the plurality of signals is outside the reference range, the operation processor determines that the cartridge is improperly mounted.

9. The analysis device of claim 1, further comprising a memory configured to store information with respect to a kind of the cartridge,
wherein the operation processor is configured to determine the mounted state of the cartridge based on the at least one measured signal and a reference, wherein the reference is set according to the information stored in the memory with respect to the kind of the cartridge.

10. The analysis device of claim 1, further comprising a display unit configured to display the mounted state of the cartridge.

11. A method of determining a mounted state of a cartridge mounted in an analysis device, the method comprising:
mounting a cartridge, on which at least one well for containing a specimen is formed, in the analysis device;
measuring at least one signal corresponding to the at least one well formed on the cartridge; and
determining a mounted state of the cartridge based on the at least one measured signal.
wherein the at least one well comprises a plurality of wells, the measuring comprises measuring a plurality of signals corresponding to the plurality of wells, and the determining comprises determining the mounted state of the cartridge based on a deviation among the plurality of measured signals.

12. The method of claim 11, wherein the at least one measured signal is at least one optical signal.

13. The method of claim 11, wherein the measuring the plurality of signals comprises:
sequentially scanning and irradiating light onto the plurality of wells; and
detecting the plurality of optical signals from the light irradiated onto the plurality of wells.

14. The method of claim 13, wherein the irradiating light onto the plurality of wells comprises irradiating light having a wavelength that is unaffected by a reagent and a specimen contained in the plurality of wells.

15. The method of claim 11, wherein the plurality of wells comprises a specimen well and a reference measurement well;
the measuring comprises measuring a signal corresponding to the specimen well and measuring a signal corresponding to the reference measurement well; and
the determining comprises determining the mounted state of the cartridge based on a deviation between the measured signal corresponding to the specimen well and the measured signal with respect to the reference measurement well.

16. The method of claim 11, wherein
the determining the mounted state of the cartridge comprises determining the mounted state based on at least one of: a difference among absolute values of the plurality of measured signals, a ratio of a maximum value of the plurality of measured signals to a minimum value of the plurality of measured signals; a difference between the maximum value of the plurality of measured signals and the minimum value of the plurality of measured signals; an average deviation of the plurality of measured signals; and a standard deviation of the plurality of measured signals.

17. The method of claim 11, wherein the measuring comprises measuring the plurality of signals corresponding to the plurality of wells, and the determining comprises determining the mounted state of the cartridge based on at least one of the plurality of measured signals.

18. The method of claim 11, wherein the determining the mounted state of the cartridge comprises determining that the cartridge is properly mounted when the deviation is within a reference range, and determining that the cartridge is improperly mounted when the deviation is outside the reference range.

19. The method of claim 11, further comprising storing, in a memory, information with respect to a kind of the cartridge;
wherein the determining the mounted state of the cartridge comprises determining the mounted state of the cartridge based on the at least one measured signal and a reference, wherein the reference is set according to the information stored in the memory with respect to the kind of the cartridge.

20. The method of claim 11, further comprising displaying the mounted state of the cartridge.

21. A method of detecting a mounted state of a cartridge, the method comprising:
irradiating light onto a plurality of wells formed on a cartridge mounted in an analysis device;
detecting light transmitted through the plurality of wells;
determining the mounted state of the cartridge based on the detected light,
wherein the detecting the light comprises measuring a first optical signal transmitted through a first one of the plurality of wells and measuring a second optical signal transmitted through a second one of the plurality of wells; and
wherein the determining the mounted state comprises determining the mounted state of the cartridge based on a comparison between the first optical signal and the second optical signal.

* * * * *